US009816131B2

(12) United States Patent
Weight et al.

(10) Patent No.: US 9,816,131 B2
(45) Date of Patent: Nov. 14, 2017

(54) PRESSURIZABLE CARTRIDGE FOR POLYMERASE CHAIN REACTIONS

(75) Inventors: Brent L. Weight, St. Geroge, UT (US); William D. Bickmore, St. George, UT (US); Darryl K. Zitting, Washington, UT (US)

(73) Assignee: DXNA LLC, St. George, UT (US)

( * ) Notice: Subject to any disclaimer, the term of this patent is extended or adjusted under 35 U.S.C. 154(b) by 1076 days.

(21) Appl. No.: 13/813,882

(22) PCT Filed: Aug. 1, 2011

(86) PCT No.: PCT/US2011/046156
§ 371 (c)(1),
(2), (4) Date: Jun. 10, 2013

(87) PCT Pub. No.: WO2012/018741
PCT Pub. Date: Feb. 9, 2012

(65) Prior Publication Data
US 2013/0295663 A1 Nov. 7, 2013

Related U.S. Application Data

(60) Provisional application No. 61/369,925, filed on Aug. 2, 2010.

(51) Int. Cl.
*B01L 1/00* (2006.01)
*B01L 3/00* (2006.01)
(Continued)

(52) U.S. Cl.
CPC .......... *C12Q 1/686* (2013.01); *B01L 3/50273* (2013.01); *B01L 3/5029* (2013.01);
(Continued)

(58) Field of Classification Search
CPC ............. B01L 3/5027; B01L 3/502738; B01L 3/502746; B01L 7/52; B01L 2200/0684
See application file for complete search history.

(56) References Cited

U.S. PATENT DOCUMENTS 3,983,006 A 9/1976 Acker et al.
4,686,606 A 8/1987 Yamada et al.
(Continued)

FOREIGN PATENT DOCUMENTS

CA 11225967 6/1982
CN 1720333 A 1/2006
(Continued)

OTHER PUBLICATIONS

PCT Application PCT/US2011/046156; filing date Aug. 1, 2011; Weight et al.; International Search Report dated Mar. 2, 2012.
(Continued)

*Primary Examiner* — Nathan Bowers
(74) *Attorney, Agent, or Firm* — Thorpe North & Western, LLP

(57) ABSTRACT

Methods and apparatus for use in connection with the performance of the polymerase chain reaction are provided. An exemplary sample processing module is described that includes a sample assembly and a PCR assembly, the sample processing module being configured to hold the sample therein at a pressure higher than ambient pressure. A sample is added to the sample assembly at the time of use, which is then connected to the PCR assembly. Embodiments of the cartridge include a flow restriction device that enables or aids in creating a higher pressure within the reaction vial. The sample is introduced into a PCR reaction vial, which contains all of the constituents of a PCR reaction mixture that are necessary to process the sample and provide amplified DNA of interest, if that DNA was present in the sample.

15 Claims, 9 Drawing Sheets

(51) Int. Cl.
*C12Q 1/68* (2006.01)
*B01L 7/00* (2006.01)

(52) U.S. Cl.
CPC ....... *B01L 3/5082* (2013.01); *B01L 3/502715* (2013.01); *B01L 3/502723* (2013.01); *B01L 7/52* (2013.01); *B01L 2200/0684* (2013.01); *B01L 2300/022* (2013.01); *B01L 2300/0681* (2013.01); *B01L 2300/123* (2013.01); *B01L 2400/0478* (2013.01)

(56) References Cited

U.S. PATENT DOCUMENTS

| | | | |
|---|---|---|---|
| 4,811,218 | A | 3/1989 | Hunkapiller et al. |
| 5,538,848 | A | 7/1996 | Livak et al. |
| 5,681,741 | A | 10/1997 | Atwood et al. |
| 5,757,014 | A | 5/1998 | Bruno et al. |
| 5,854,684 | A | 12/1998 | Stabile et al. |
| 5,935,522 | A | 8/1999 | Swerdlow et al. |
| 5,935,524 | A | 8/1999 | Bass et al. |
| 5,985,651 | A | 11/1999 | Hunicke-Smith |
| 6,015,674 | A | 1/2000 | Woudenberg et al. |
| 6,027,695 | A | 2/2000 | Oldenburg et al. |
| 6,174,670 | B1 | 1/2001 | Wittwer et al. |
| 6,180,372 | B1 | 1/2001 | Franzen |
| 6,303,288 | B1 | 10/2001 | Furcht et al. |
| 6,369,893 | B1 | 4/2002 | Christel et al. |
| 6,395,504 | B1 | 5/2002 | Trudil |
| 6,399,397 | B1 | 6/2002 | Zarling et al. |
| 6,558,947 | B1 | 5/2003 | Lund et al. |
| 6,597,450 | B1 | 7/2003 | Andrews et al. |
| 6,605,475 | B1 | 8/2003 | Taylor et al. |
| 6,652,809 | B1 | 11/2003 | Comley et al. |
| 6,814,934 | B1 | 11/2004 | Higuchi |
| 6,838,680 | B2 | 1/2005 | Maher et al. |
| 6,852,986 | B1 | 2/2005 | Lee et al. |
| 6,875,619 | B2 | 4/2005 | Blackburn |
| 6,881,962 | B2 | 4/2005 | Kamijo et al. |
| 6,912,050 | B2 | 6/2005 | Inberg |
| 6,914,677 | B2 | 7/2005 | Mader et al. |
| 7,119,345 | B2 | 10/2006 | King |
| 7,122,799 | B2 | 10/2006 | Hsieh et al. |
| 7,315,376 | B2 | 1/2008 | Bickmore, Jr. et al. |
| 7,332,347 | B2 | 2/2008 | Li et al. |
| 7,939,312 | B2 | 5/2011 | Roberts et al. |
| 8,829,473 | B1* | 9/2014 | Griswold ............... B01L 3/545 250/458.1 |
| 2001/0000752 | A1 | 5/2001 | Franzen |
| 2001/0012612 | A1* | 8/2001 | Petersen ............... B01L 3/502 435/5 |
| 2002/0001539 | A1 | 1/2002 | DiCesare et al. |
| 2003/0013188 | A1 | 1/2003 | Dumas |
| 2004/0043479 | A1 | 3/2004 | Briscoe et al. |
| 2004/0043502 | A1 | 3/2004 | Song et al. |
| 2004/0119974 | A1 | 6/2004 | Bishop et al. |
| 2004/0178357 | A1 | 9/2004 | King |
| 2004/0214200 | A1 | 10/2004 | Brown et al. |
| 2006/0019274 | A1 | 1/2006 | Goel |
| 2006/0068499 | A1 | 3/2006 | Wohlstadter et al. |
| 2006/0188891 | A1 | 8/2006 | Bickmore, Jr. et al. |
| 2007/0031495 | A1 | 2/2007 | Eppstein et al. |
| 2007/0231851 | A1 | 10/2007 | Toner et al. |
| 2008/0050781 | A1 | 2/2008 | Oldham et al. |
| 2008/0056948 | A1 | 3/2008 | Dale et al. |
| 2008/0085541 | A1 | 4/2008 | Spangler |
| 2008/0190220 | A1 | 8/2008 | Backes et al. |
| 2008/0248586 | A1 | 10/2008 | Tajima |
| 2008/0254517 | A1 | 10/2008 | Mortillaro et al. |
| 2009/0130719 | A1 | 5/2009 | Handique |
| 2009/0165876 | A1* | 7/2009 | Atkin ............... B01L 3/502723 137/825 |
| 2009/0321259 | A1 | 12/2009 | Vann et al. |
| 2010/0037677 | A1 | 2/2010 | Lee et al. |
| 2011/0009291 | A1 | 1/2011 | Chen et al. |
| 2012/0288897 | A1* | 11/2012 | Ching ............... B01F 11/0071 435/91.2 |

FOREIGN PATENT DOCUMENTS

| | | |
|---|---|---|
| CN | 101262948 A | 9/2008 |
| CN | 101715429 A | 5/2010 |
| JP | 2005-117987 | 5/2005 |
| JP | 2010-30925 A | 6/2010 |
| JP | 2010130925 | 6/2010 |
| WO | WO 2006/132666 A | 12/2006 |
| WO | WO 2008/027398 A3 | 3/2008 |
| WO | WO 2008/045431 A2 | 4/2008 |
| WO | WO 2008/143959 A1 | 11/2008 |
| WO | WO 2009/037518 A1 | 5/2009 |
| WO | WO 2009/067518 A1 | 5/2009 |

OTHER PUBLICATIONS

PCT Application PCT/US2007/18946; filing date Aug. 28, 2007; Advanced Molecular Systems, LLC; International Search Report dated Sep. 17, 2008.

PCT Application PCT/US07/21567; filing date Oct. 9, 2007; F.L. Spangler, Jr.; International Search Report dated Aug. 5, 2008.

PCT Application PCT/US07/21567; filing date Oct. 9, 2007; F.L. Spangler, Jr.; Written Opinion of the International Searching Authority dated Aug. 5, 2008.

U.S. Appl. No. 61/369,925, filed Aug. 2, 2010; Brent L. Weight.

U.S. Appl. No. 11/958,332, filed Dec. 17, 2007; Danvern R. Roberts.

U.S. Appl. No. 11/958,299, filed Dec. 17, 2007; Danvern R. Roberts.

* cited by examiner

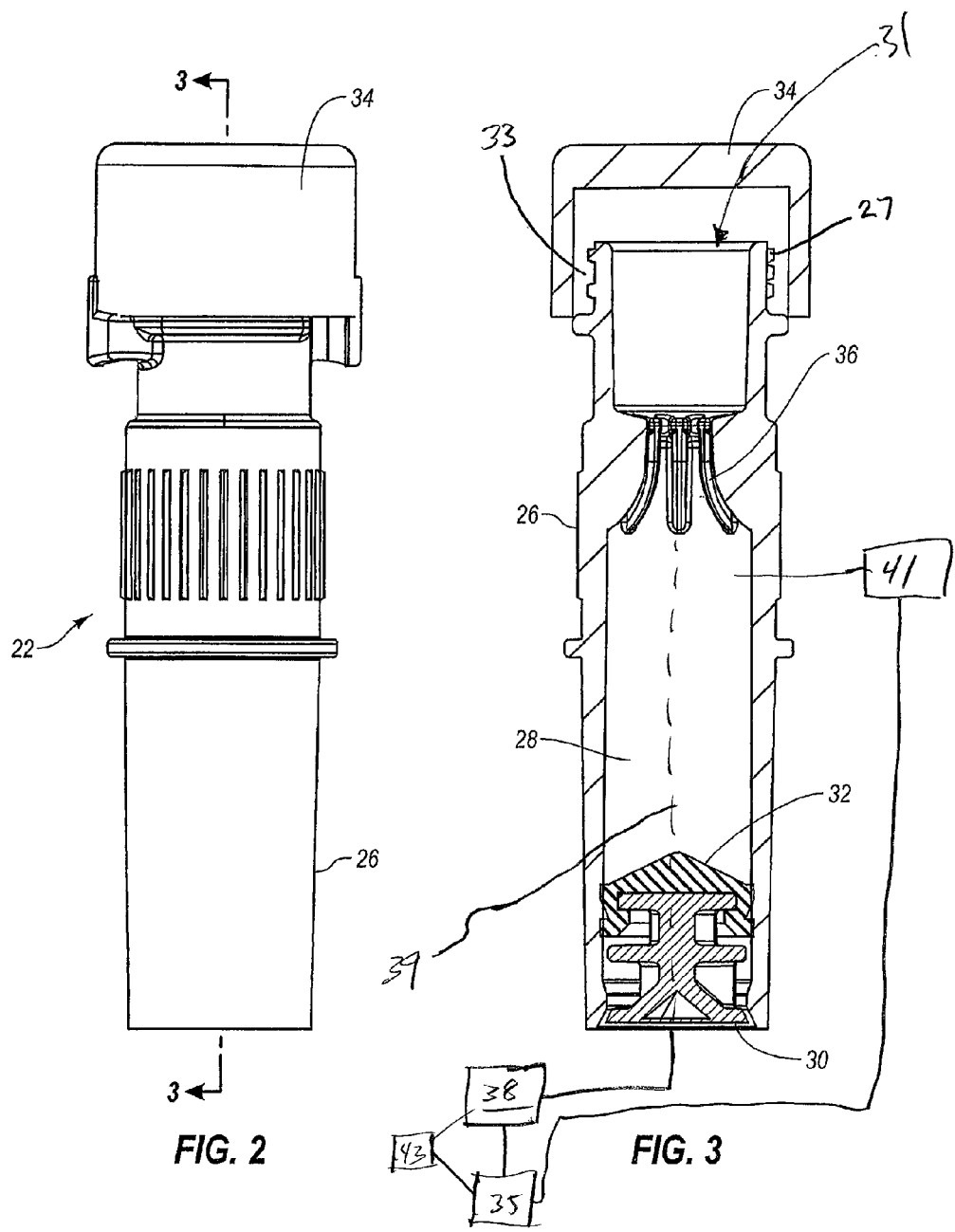

PRESSURIZABLE CARTRIDGE FOR POLYMERASE CHAIN REACTIONS

CROSS-REFERENCE TO RELATED APPLICATIONS

This application claims the benefit of U.S. Provisional Application No. 61/369,925 filed Aug. 2, 2010, the entirety of which is incorporated herein by this reference for all purposes.

BACKGROUND OF THE INVENTION

1. The Field of the Invention

The present invention is directed to the field of thermocyclers used in the practice of the polymerase chain reaction (PCR).

2. The Relevant Technology

An important tool in the field of molecular biology is the process known as the "polymerase chain reaction" (PCR). PCR generates large quantities of genetic material from small samples of the genetic material.

The PCR process is performed in a small reaction vial containing components for DNA duplication: the DNA to be duplicated, and PCR reaction agents that include the four nucleotides which are assembled to form DNA, two different types of synthetic DNA called "primers" (one for each of the complementary strands of DNA), and an enzyme called DNA polymerase, typically entrained in a carrier fluid.

DNA is double stranded. The PCR process begins by separating the two strands of DNA into individual complementary strands, a step which is referred to as "denaturation." This is typically accomplished by heating the PCR reaction mixture to a temperature of about 94 to about 96 degrees centigrade for a period of time between a few seconds to over a minute in duration.

Once the DNA is separated into single strands, the mixture is cooled to about 45 to about 60 degrees centigrade (typically chosen to be about 5 degrees below the temperature at which the primer will melt) in order to allow a primer to bind to each of the corresponding single strands of DNA in the mixture. This step is typically called "annealing." The annealing step typically takes anywhere from a few seconds up to a few minutes.

Next, the reaction vessel is heated to about 72 to 73 degrees centigrade, a temperature at which DNA polymerase in the reaction mixture acts to build a second strand of DNA onto the single strand by adding nucleic acids onto the primer so as to form a double stranded DNA that is identical to that of the original strand of DNA. This step is generally called "extension." The extension step generally takes from a few seconds to a couple minutes to complete.

This series of three steps, also sometimes referred to as "stages", define one "cycle." Completion of a PCR cycle results in doubling the amount of DNA in the reaction vial. Repeating a cycle results in another doubling of the amount of DNA in the reaction vial. Typically, the process is repeated many times, e.g. 10 to 40 times, resulting in a large number of identical pieces of DNA. Performing 20 cycles results in more than a million copies of the original DNA sample. Performing 30 cycles results in more than a billion copies of the original DNA sample. A "thermocycler" is used to automate the process of moving the reaction vessel between the desired temperatures for the desired period of time.

DNA for amplification must be obtained from a biological sample, which involves disrupting biological tissues, cell walls, capsids, or the like, in order to release a particular DNA of interest. In some instances, a particular RNA is of interest, although the RNA must be converted to DNA in order to use PCR for amplification.

A challenge in managing PCR reactions occurs when the temperature range at which denaturation takes places is near the boiling temperature of the carrier fluid. For example, at higher altitudes such as might be found in cities like Denver, water, a typical carrier fluid, boils at 97 degrees centigrade. Heating a sample from about 94 to about 96 degrees centigrade may cause bubbles of water vapor and/or dissolved gases to form. These bubbles pose a challenge during PCR, particularly those systems that rely upon optical detection systems. That is, optical detection systems project an optical signal through the reaction vessel and the sample. Bubbles, however, can at least partially occlude and/or distort and/or refract the optical signal and, in so doing, degrade the signal quality and/or introduce noise received at the optical detector. Prior art solutions attempted to resolve this problem by using very precise and, consequently, very expensive thermal controls to try and prevent boiling from occurring, often with limited success.

Bubbles may also be present before the thermocycling process, such as those that develop in what can be turbulent flow of the sample as it flows into the reaction vessel or pockets of gas that become trapped within the reaction vessel when the sample enters the reaction vessel. Such bubbles pose the same problems as those generated during thermocycling.

In addition, the presence and development of bubbles within the fluid alters the volume of the fluid. This occurs as the volume of the bubbles change much more significantly than the volume of the fluid and sample change during thermocycling. The change in the volume of the bubbles cause the fluid and entrained DNA sample to flow in and out of the reaction vessel. Such flows of the fluid in and out of the reaction vessel may alter and/or dilute the concentration of the DNA sample and/or the PCR reaction agents within the reaction vessel.

Thus, there exists a need for a PCR process and system that improves signal quality. In addition, there exists a need for a PCR system that reduces the presence of bubbles within the sample.

BRIEF SUMMARY OF THE INVENTION

Conventional PCR systems and methodology require the use of laboratory equipment and skilled technicians. The present invention is directed to methods and apparatus that can lessen the requirements for laboratory equipment and for skilled technicians and can even be used in applications in the field outside the presence of skilled technicians.

An exemplary sample processing module is described that includes a sample assembly and a PCR assembly. A sample is added to the sample assembly at the time of use, which is then connected to the PCR assembly. The sample is introduced into a PCR reaction vial within the PCR assembly, which contains all of the constituents of a PCR reaction mixture that are necessary to process the sample and provide amplified DNA of interest, if that DNA was present in the sample.

Embodiments of the invention include those in which a sample within the PCR reaction vial assembly can be pressurized above ambient pressure through the use of a flow restriction device. The flow restriction device is in fluidic communication with at least one PCR reaction vial. An embodiment of the flow restriction device includes a permeable membrane that at least partially permits at least a first fluid to pass through the membrane and at least partially prevents at least a second fluid from flowing through the membrane. Another embodiment of the flow restriction device includes various types of valves.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It should be understood that these drawings depict only typical embodiments of the invention and are therefore not to be considered limiting of its scope. The invention will be described and explained with additional specificity and detail through the use of the accompanying drawings in which:

FIG. 2 is a side view of a sample assembly.

FIG. 3 is a cross-sectional side view taken along section line 3-3 of FIG. 2.

DETAILED DESCRIPTION

The polymerase chain reaction is an important tool for use as a precursor for a number of activities, such as the identification of small amounts of a particular genetic material in a sample, measurement of how much genetic material is present in a sample, or generation of enough genetic material for use in various applications.

Conventional thermocyclers have taken a number of forms. The most common thermocyclers utilize a plurality of sample vials placed into a large, solid, thermally conductive block. Each vial is manually loaded with sample DNA desired to be amplified, hereinafter sometimes referred to as "template DNA," and the chemical constituents necessary for the polymerase chain reaction. The steps of the PCR process are performed in a laboratory by skilled technicians.

Figure 1:
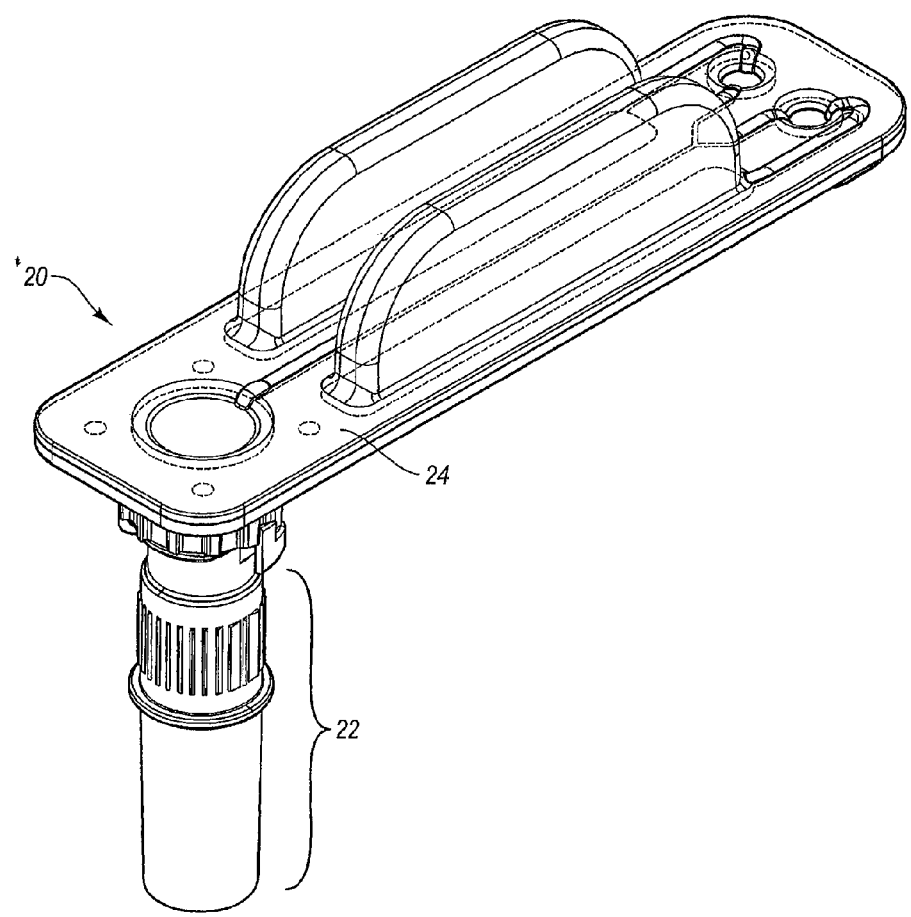
FIG. 1 is a perspective view of an embodiment of a sample processing module.

Referring to FIG. 1, the present invention provides a sample processing module 20 which simplifies the PCR process, various aspects of which are disclosed in the co-pending U.S. patent application Ser. No. 11/958,332, filed Dec. 17, 2007 and entitled "PCR Sample Processing Module," which is incorporated in its entirety for all purposes by this reference. Sample processing module 20 comprises a sample assembly 22 and a PCR assembly 24. Sample assembly 22 is used for collection and optional processing of a biological sample, template DNA, or a template RNA. PCR assembly 24 is used for the performance of PCR amplification of template DNA.

FIG. 2 is a side view of sample assembly 22 prior to being attached to PCR assembly 24. As more easily seen in the cross-sectional view of sample assembly 22 taken along section line 3-3 of FIG. 2, FIG. 3 shows sample assembly 22 as having a body 26 which contains an interior cylindrical cavity 28 with an open end 31 for receiving a sample of a biological material or a solution, such as a carrier fluid, containing template DNA or RNA. Sample assembly 22 is advantageously provided with a removable threaded cap 34 having cap threads 33 that mates with corresponding body threads 27 on the body 26 of the sample assembly 22 so as to protect cavity 28 from contamination prior to use and to secure the contents once a sample is placed within the cavity 28 but prior to the sample assembly 22 being secured to the PCR assembly 24. Of course, other ways of mating the body 26 to the cap 34 and the PCR assembly 24 can be used, such as friction fits, seals, clasps, latches, and the like, all fall within the scope of the disclosure. The upper end of cavity 28 may be provided with an anti-splash structure 36.

The bottom end of cavity 28 is sealed by a movable plug 30, which on its upper end is fitted with a seal 32 that prevents escape of the contents of the cavity. The movable plug 30 is mechanically coupled to a linear actuator 38 that moves the moveable plug 30 into and out of the cavity 28 along axis 39. In some embodiments, the linear actuator is actuated manually, such as by a user depressing a plunger (not shown). In other embodiments, the linear actuator 38 is connected to a controller 35 that generates a movement signal and transmits it to the linear actuator 38, that may include any of various types of electric motors, screw drives, and equivalent systems. The controller 35 can be a general purpose computer with a program written to effect the described actions and/or it may be a specific instruction computer or chip. Optionally, the controller 35 stops sending the movement signal and/or transmits a stop signal after a given period of time, during which the distance traveled may be calculated for the rate at which a linear actuator 38 moves the moveable plug 30.

Optionally, a pressure sensor 41 operably coupled to the sample assembly 22 and/or the PCR assembly 24 (FIG. 8) is coupled to the controller 35. The pressure sensor 41 is configured to generate a pressure signal reflective of the pressure in the cavity 28 and/or one or more areas of the PCR assembly 24, such as the PCR reaction vial 56 (FIG. 8) and transmit the pressure signal to the controller 35. The controller 35, in response to a pressure signal, stops sending the movement signal and/or transmits a stop signal to the linear actuator 38. Optionally, a force gauge 43 configured to detect a force applied by the linear actuator 38 to the moveable plug 30 and to generate a force signal representative of the force is coupled to the controller 35. Embodiments of the force gauge include electrical, electro-mechanical, mechanical switches, and binary devices that change state when a selected or target force is met. The force gauge 43 transmits the force signal to the controller 35. The controller 35, in response to the force signal, stops sending the movement signal and/or transmits a stop signal to the linear actuator 38.

Figure 15:
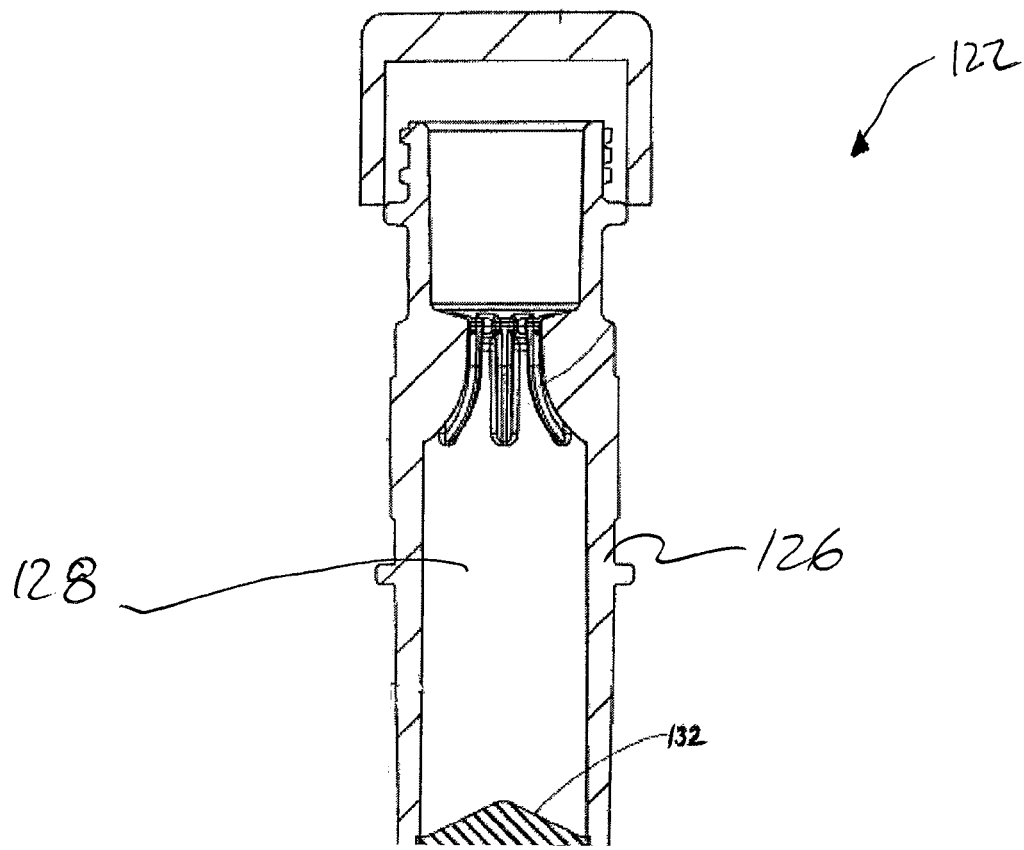
FIG. 15 is a cross-sectional side view of another embodiment of a sample assembly taken along section line 3-3 of FIG. 2.

Rather than a moveable plug 30, another embodiment of sample assembly 122 illustrated in FIG. 15 includes a flexible membrane or bladder 132 incorporate or mechanically coupled to the body 126 of the sample assembly 122. The flexible membrane 132 acts similarly to the moveable plug 30 in that it is deflected inward into the cavity 128 of the sample assembly 122 and, in so doing, urges the sample into the PCR assembly 24 as described below. A possible advantage of using a flexible membrane 132 is that it may reduce the risk of a leak occurring at higher pressures at the interface where the flexible membrane 132 couples to the body 126 as compared to the seal provided by the moveable plug 30 against the body 26. The flexible membrane 132 may be deflected inward through the use of air pressure or other force applied to the flexible membrane 132 as an alternative to the linear actuator 38.

Figures 4, 5:
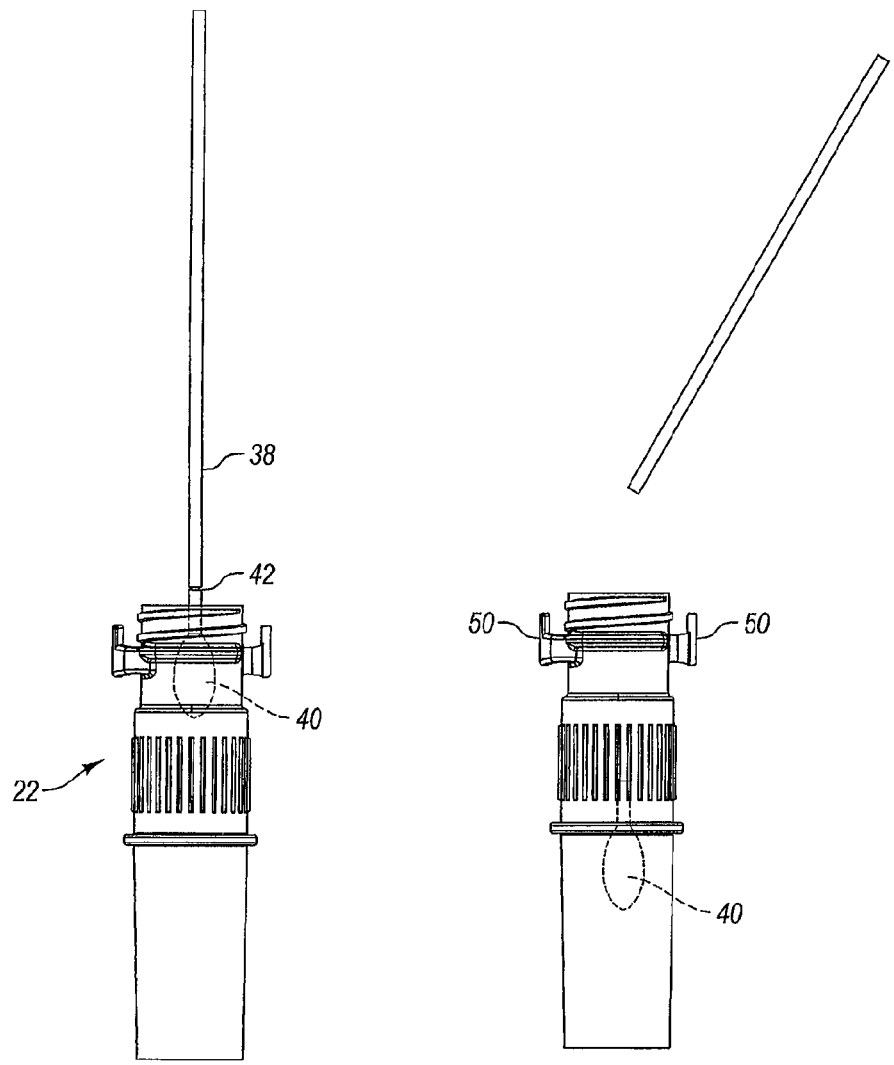
FIG. 4 is a side view of the sample assembly of FIG. 2 and a swab.
FIG. 5 is another side view of the sample assembly of FIG. 2 and a swab.

Sample assembly 22 may be preloaded with a solution or dried constituents, reagents, base chemicals, such as deoxyribonucleic triphosphate (dNTP), and the like, or may be provided empty until use. Although a template DNA may be placed into the sample assembly 22 for use with the PCR sample processing module 20, it is contemplated that the sample assembly 22 can utilize intact biological samples. FIGS. 4 and 5 depict the use of a swab 38 which has been used to collect a biological sample, for example from a patient's throat. Swab tip 40 may be separated from the swab 38 at a weakened area 42, allowing swab tip 40 to drop into cavity 28 of the sample assembly 22. The sample assembly 22 may then be subjected to an ultrasonic treatment to release DNA and RNA from the biological sample in accordance with the methods and apparatus of copending U.S. patent application Ser. No. 11/958,299, filed Dec. 17, 2007 and entitled "Ultrasonic Release of DNA and RNA," the disclosure of which is incorporated herein by reference in its entirety for all purposes.

Figure 6:
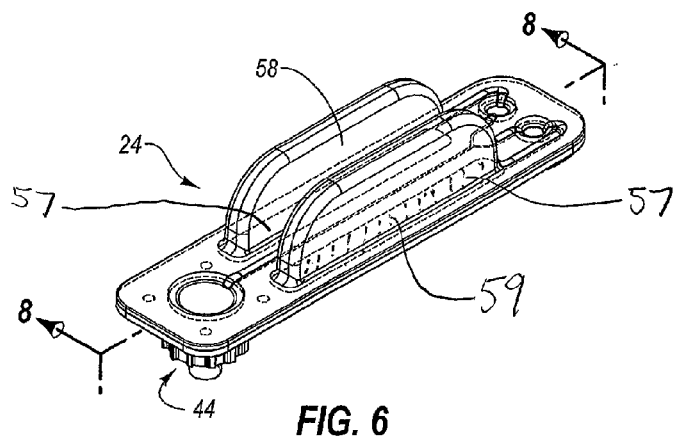
FIG. 6 is a perspective view of a PCR assembly.
Figure 7:
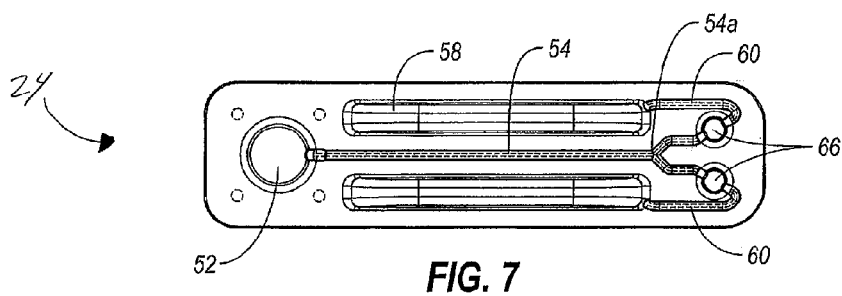
FIG. 7 is a top view of the PCR assembly of FIG. 6.
Figure 8:
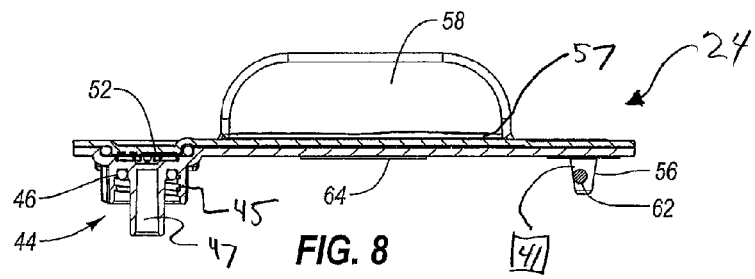
FIG. 8 is a cross sectional side view of the PCR assembly of FIG. 6.

FIGS. 6-9 and 11-13 depict different views of the PCR assembly 24 of FIG. 1. PCR assembly 24 is provided with a interface 44 that mates with the open end 31 and the body threads 27 of the sample assembly 22 illustrated best in FIG. 3. As best seen in FIG. 8, a sealing element 46, such as an O-ring, rubber gasket, and the like, is provided to act as a seal between the PCR assembly 24 and sample assembly 22.

Figure 9:
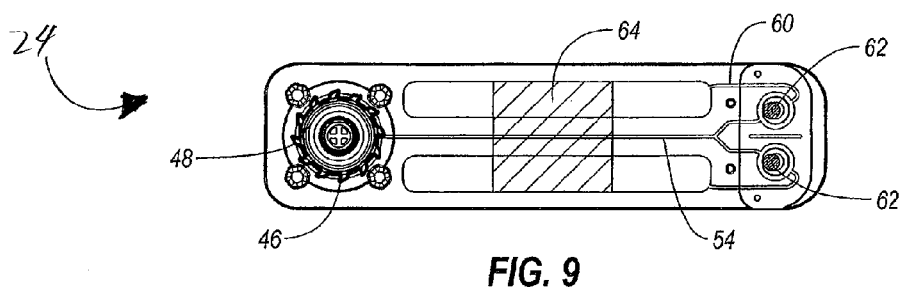
FIG. 9 is a bottom view of the PCR assembly of FIG. 6.

It is preferred that interface 44 and the sample assembly 22 be provided with a locking structure 48, illustrated in FIG. 9, that prevents the sample assembly 22 from being removed once it has been secured to the PCR assembly 24 so as to protect against subsequent exposure of the contents of the sample assembly to users or handlers of the sample processing module 20, a feature that is particularly desirable when working with virulent substances. The locking structure 48, for example, optionally includes ratchet notches that interface with flanges 50 on the sample assembly 22 (see FIG. 5) so as to allow sealing attachment of the sample assembly 22 to the PCR assembly 24, but to thereafter prevent removal of the sample assembly 22 from the PCR assembly 24.

A fluid conduit 47 in the PCR assembly 24 provides a route through which fluids and the sample contained within the cavity 28 of the sample assembly 22 travel. A filter 52 is provided over the fluid conduit 47 to prevent solid matter from passing from the sample assembly 22 into a fluid delivery channel 54 of the PCR assembly 24. Stated differently, solution containing template DNA to be amplified contained within the cavity 28 of the sample assembly 22 is urged through the filter 52 and into the delivery channel 54 by raising the movable plug 30 upwardly into cavity 28 so as to eject the solution from the cavity 28 into the delivery channel 54. Delivery channel 54 carries sample solution from the sample assembly 22 to one or more PCR reaction vials 56. The illustrated PCR assembly 24 shows the use of two PCR reaction vials 56, each of which is provided with sample via a split in the delivery channel 54 shown at reference numeral 54a.

It is preferred that the sample processing module 20 be permanently secured in place following attachment of the sample assembly 22 to the PCR assembly 24 so as to protect against release of potentially hazardous materials. Inasmuch as this results in an enclosed, non-vented space which decreases in overall volume as the movable plug is advanced within cavity 28, it is preferred to provide one or more air chambers that serve to accommodate the reduction of volume without impeding flow of solution from the sample assembly 22 to the PCR reaction vials 45, and which also serve as a vent location for bubbles forming within the PCR reaction vials 56. The illustrated embodiment utilizes vent chambers 58 for this purpose, which communicate with PCR reaction vials 56 through vent channels 60 but which are otherwise sealed.

Figure 14:
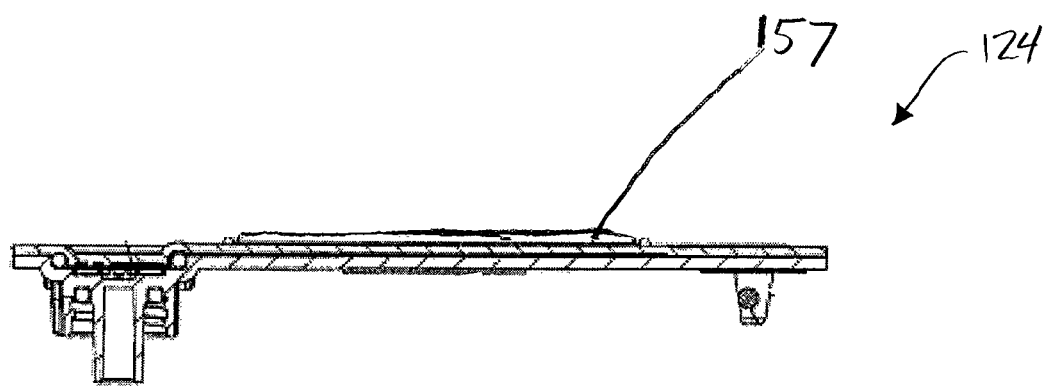
FIG. 14 is a cross-sectional view of another embodiment of a PCR assembly.

Although FIGS. 6-9 show use of a separate vent chamber 58 for each of the PCR reaction vials 56, it should be understood that this is not required and that other configurations could provide the same functionality as vent chambers 58. For example, and as will be discussed below, embodiments of the PCR assembly 124 illustrated in FIG. 14 optionally forego a vent chamber altogether and provide a structure through which gases might be vented directly to the atmosphere.

It is preferred that each PCR reaction vial 56 contain a lyophilized bead 62 comprising the various constituents, hereinafter "the PCR reaction mixture," required to amplify the template DNA supplied from the sample assembly 22. The PCR reaction mixture within the lyophilized bead 62 will include the primers necessary to amplify the template DNA, the polymerase, dNTP, and any other necessary constituents. More than one lyophilized bead 62 may be provided if that is more convenient or if various constituents of the PCR reaction mixture need to be isolated from one another prior to use.

The PCR reaction mixture will differ depending on the template DNA to be amplified. Inasmuch as PCR assembly 24 is provided in a preloaded form factor, a label should be attached which identifies the preloaded PCR assembly. FIGS. 8 and 9 show the use of a radio frequency identification (RFID) label 64, which can also be used to provide information to a thermocycler with which the sample module is used. Optimal operating conditions and protocols, such as those used by the controller 35 may differ depending upon the template DNA or the constituents of the PCR reaction mixture, so the RFID identification information can also be used to select a thermocycler program, which may include instructions regarding parameters such as target temperatures and cycle times, that are optimal for the contents of the PCR reaction mixture.

Figure 10:
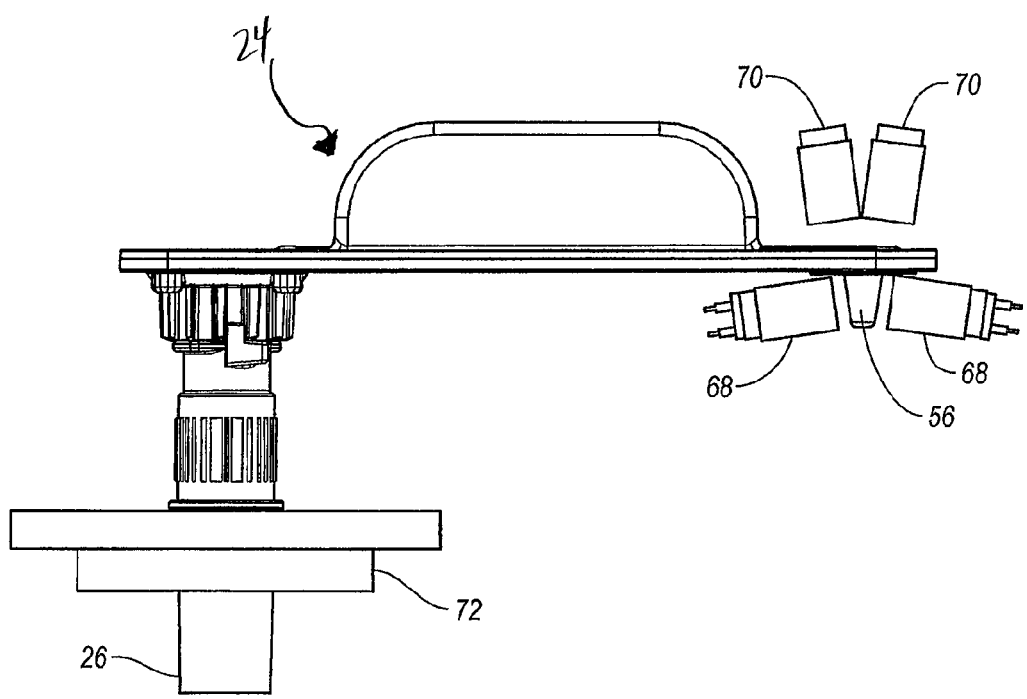
FIG. 10 is a side view of the sample processing module of FIG. 1 and optional associated structures.

It is preferred that PCR be monitored and controlled on a real time basis. FIG. 7 depicts the provision of lenses 66 to assist in direct visual observation of the contents of PCR reaction vials 56. FIG. 10 depicts the use of optical excitation sources 68 for use in the excitation of fluorescent constituents of the PCR reaction mixture, and photo receivers 70 which monitor fluorescent emissions through lenses 66. Copending U.S. Patent Application Publication Application No. US 2006/0152727, entitled "Fluorescence Detection System," incorporated in its entirety by this reference for all purposes, contains additional details of fluorescent detection systems that could be implemented for use with PCR assembly 24. Copending U.S. Patent Application Publication No. US 2006/018889, entitled "Methods and Apparatus for Controlling DNA Amplification," incorporated in its entirety by this reference for all purposes, provides information regarding the control of PCR using real time information from an optical detection system.

As noted, bubbles may form with the sample and the carrier fluid during the filling of the reaction vials 56 and/or during the thermocycling process, particularly if the vapor pressure of the sample and carrier fluid is close to the temperature at which the denaturing process occurs, thereby raising the risk of unintentionally boiling the sample. For example, an ideal denaturing temperature for a typically is from about 94 degree centigrade to about 96 degrees centigrade. However, the boiling point of water at a city at the altitude of Denver, Colo., for example, is at about 97 degrees centigrade. Thus, to avoid unintentionally boiling the sample during a PCR reaction occurring in Denver requires the use of very accurate and, consequently, expensive thermal control system. In addition, bubbles of dissolved gases might come out of solution during the thermocycling process as the capacity of the carrier fluid to maintain the dissolved gases in solution decreases during the heating phase of the thermocycle. Further, the presence and development of bubbles within the fluid alters the volume of the fluid. This occurs as the volume of the bubbles change much more significantly than the volume of the fluid and sample change during thermocycling. The change in the volume of the bubbles cause the fluid and entrained DNA sample to flow in and out of the reaction vessel. Such flows of the fluid in and out of the reaction vessel may alter and/or dilute the concentration of the DNA sample and/or the PCR reaction agents with in the reaction vessel.

These bubbles pose several potential difficulties in accurately replicating and analyzing samples that undergo a PCR reaction. For one, it has been discovered that bubbles often form under lenses 66, and these bubbles can result in inaccurate readings by photo receivers 70.

Figure 11:
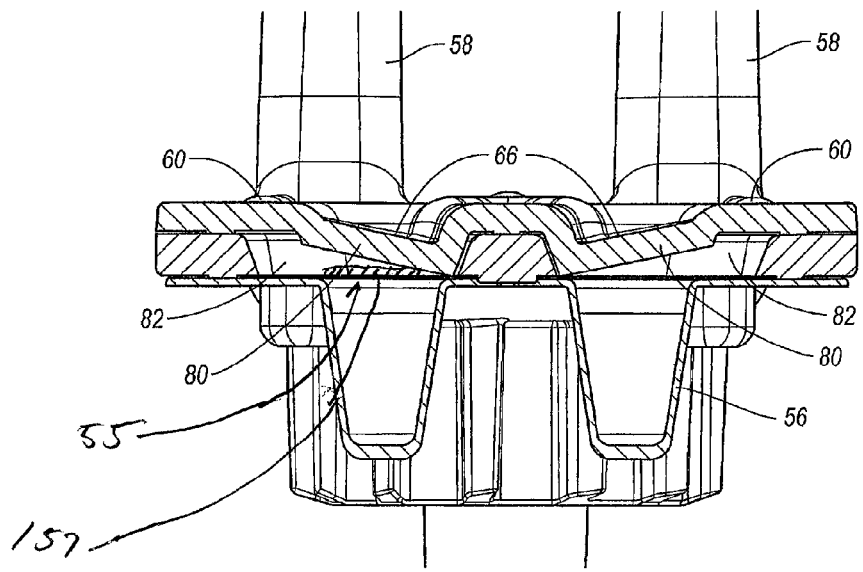
FIG. 11 is a partial cross-sectional view of an embodiment of the PCR assembly of FIG. 6.
Figure 12:
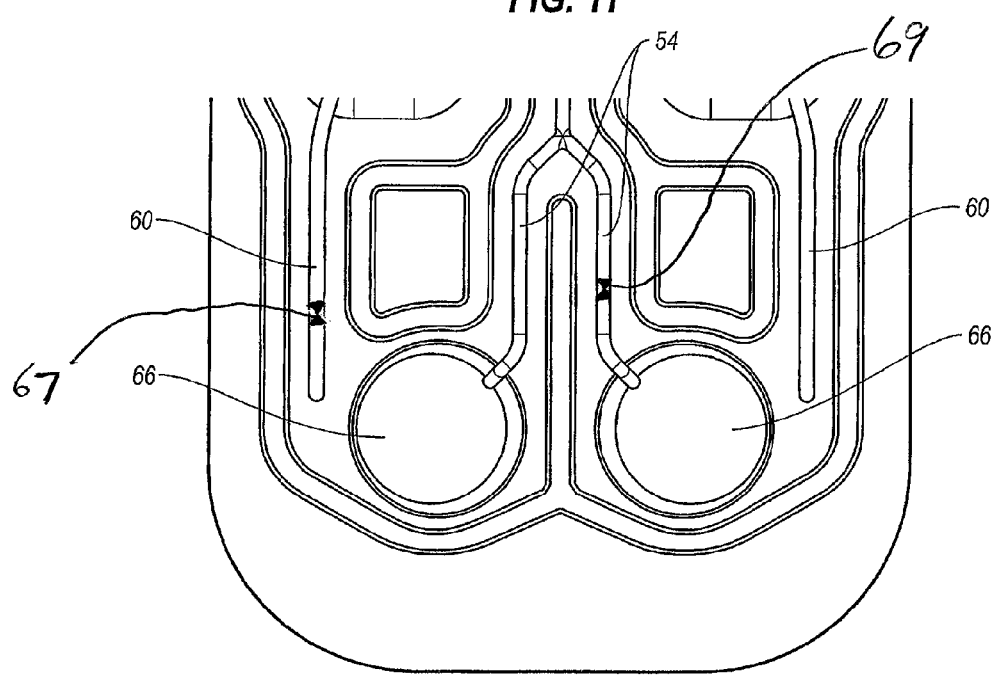
FIG. 12 is a partial top view of the lenses and surrounding components of the PCR assembly of FIG. 6.
Figure 13:
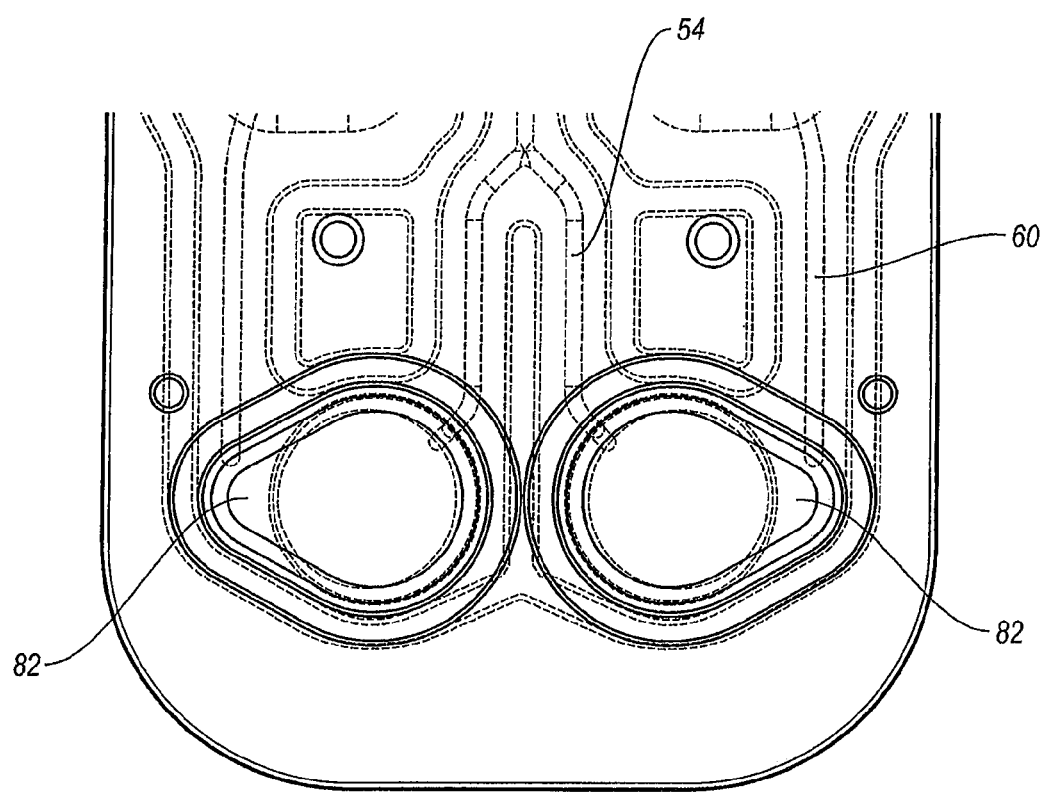
FIG. 13 is a bottom view corresponding to FIG. 12.

To manage and mitigate the effect any bubbles might have after the bubbles have developed, FIGS. 11-13 depict a configuration of lenses 66 and associated structure which is useful to direct bubbles away from the lenses so that the accuracy of readings is not impeded. FIG. 11 shows the use of an angled portion 80 formed in the structure of the PCR assembly overlying reaction vials 56. This angled portion 80 serves to direct bubbles away from the area underlying the lenses 66, and toward connecting vent channels 60 which lead to vent chambers 58. As best seen by reference to both FIGS. 11 and 13, using a teardrop shaped cavity 82 further assists in directing bubbles toward vent channels 60.

While the angled portion 80 acts to shepherd and guide bubbles away from the lenses 66 after the bubbles form, it is desirable to reduce the number of bubbles generated, in the first instance. Further, it is desirable to reduce the volume of any individual bubble after the bubble has formed. In so doing, the efficacy of the angled portion 80 to shepherd or guide bubbles that are created could possibly be improved.

Applicants have discovered that including an optional flow restriction device 57 (FIGS. 6 and 8) downstream of the reaction vials 56 and between the reaction vials 56 and the vent chambers 58. In one embodiment, the flow restriction device 57 in FIGS. 6 and 8 is a permeable membrane that is sealed, such as by welding by heat, laser, sonically, and the like, to the PCR assembly 24. In the embodiment illustrated in FIGS. 6 and 8, each permeable membrane 57 is substantially the same length and width of the associated vent chamber 58. Of course, it will be understood that the dimensions of the permeable membrane 57 may be selected as appropriate. In addition, the location of the permeable membrane can be located in different locations, including within an inner diameter of the vent channel 60.

In another embodiments, the permeable membrane 157 may form at least a portion of a wall 55 of the reaction vial 56, as illustrated in FIG. 11. An advantage of the embodiment in which the permeable membrane 157 forms a portion of a wall 55 is that it may prevent PCR reagents, the sample, and/or the carrier fluid from being flushed or diluted out of the reaction vials 56 during the filling and/or pressurization process. Further, any bubbles that do come out of solution may pass through the permeable membrane and into the vent channel 60.

An attribute of embodiments of the permeable membrane 57 is that it is selectively permeable. That is, the permeable membrane 57 is permeable to selected fluids, such as water vapor and formerly dissolved gases that come out of solution of the sample and carrier fluid. At the same time, the permeable membrane resists and/or prevents the flow of other fluids, such as water, the carrier fluid, and other liquids from passing through the permeable membrane 57. As a result, gases can flow through the permeable membrane 57 and into the vent chamber 58 while the sample and carrier fluid are retained within the reaction vial 56 and, depending upon the location of the permeable membrane 57, the vent channel 60.

Optionally, the membrane 57 and other embodiments thereof, include a framework or structure 59 to minimize or reduce any bulging or deflection of the permeable membrane 57 when a pressure differential exists between the two sides of the permeable membrane 57, as illustrated in FIG. 6. A deflection of the permeable membrane 57, if unchecked, may cause a distortion or change in the relative volumes of the vent chamber 58 and the volume upstream of the vent chamber 58 (i.e., the reaction vials 56 and associated fluid channels). That is, as the permeable membrane 57 bulges more of the carrier fluid and sample flows through the reaction vial 56, possibly causing more of any PCR reagents being flushed out of the reaction vials 56 and into the vent channel 60. Such a change in the relative volume could require a higher or lower fluid pressure and, consequently, more or less fluid than anticipated to obtain a selected pressure. Thus, a framework or supporting structure 59, such as ribs or a lattice, optionally is inserted within the permeable membrane or on one or both sides of the permeable membrane 57. The supporting structure 59 resists the deflection of the permeable membrane 57 when it is subject to a pressure differential between its two sides. In some embodiments, rather than a physical structure 59 the permeable membrane 57 optionally includes a matrix of load supporting fibers and other similar enhancements that improve the resilience and stiffness of the permeable membrane.

Another embodiment of a flow restriction device is a valve 67 located within the vent channel 60 and, optionally, valve 69 located within fluid delivery channel 54, illustrated in FIG. 12. The valve may be selectively operated by a user or under command from a controller 35 to open partially and/or fully and to selectively close the valve. Closing the valve 67 after any gases have been vented to the vent chamber 58 allows a pressure above ambient to be applied to the sample within the reaction vial 56 as will be described in further detail below. An embodiment of the valve includes those made from elastomeric elements The flow restriction device allows a pressure to be applied to the sample and carrier fluid contained within the reaction vial 56. That is, the pressure within the reaction vial 56 can be maintained above ambient pressure, such as from about atmospheric/ambient pressure to about 80 pounds per square inch (psi) above ambient pressure and, in some embodiments, pressures even higher. In other embodiments, the flow restriction device provides the capability of maintaining the pressure within the reaction vial from about 15 psi to about 60 psi above ambient pressure.

In the embodiment of the flow restriction device that comprises the permeable membrane 57, pressure is provided in the following way. As noted, the moveable plug 30 is moved linearly, urging the sample and entrained carrier fluid to flow through the fluid delivery channel 54, into the reaction vials 56, through the vent channel 60 until it reaches the permeable membrane 57. Gases, air, and other bubbles within the sample and carrier fluid will pass through the permeable membrane, while the sample and carrier fluid presses against the permeable membrane 57. Pressure above ambient can be created within the reaction vials 56 by causing the moveable plug 30 to further advance. As discussed above, the movement of the moveable plug 30 can be controlled by the controller in response to a force signal or a pressure signal, whether at the sample assembly 22 and/or the reaction vial 56. Stated differently, pressurizing the fluid against the permeable membrane 57 serves as a method to detect when a selected volume or amount of the sample and carrier fluid has entered the reaction vial 56 because any gases would have permeated the permeable membrane 57 and entered the vent chamber 58. When this occurs and the fluid reaches the permeable membrane 57 and fails to pass through the permeable membrane, a detectable increase in the pressure occurs quickly. In some instances, the pressure increase might be quite abrupt, thus indicating that the PCR assembly 24 is adequately filled to perform the PCR reaction. Thus, the rise in pressure serves, in part, as a method to detect when the sample and carrier fluid has reached the permeable membrane 57.

Another benefit of pressurizing the sample and carrier fluid against the permeable membrane 57 is that the stability of the pressure and/or force measured serves as a method of detecting leaks. That is, if the pressure and/or force measured at the moveable plug 30 were to decrease would be an indicator suggestive of a leak allowing fluid to escape from at least one of the sample assembly 22 and PCR assembly 24. Such an indication would permit a user to investigate the cause, run a new sample, and/or take other supplemental measures, particularly if the sample to be tested is hazardous.

In addition, the volume of the vent chambers 58 may be adjusted in part, to obtain a desired pressure within the reaction vial 56 and the pressure created within the vent chamber 58 by any gas that migrates into the vent chamber 58. That is, in some embodiments, the volume of the vent chamber 58 is a function of the dimensions of the cavity 28 of the sample assembly 22 and the reaction vial 56, and a desired or selected pressure to be obtained in the vent chamber 58 and the reaction vial 56, as well as the type of sample and carrier fluid as well as the reaction to occur within the reaction vessel. By calibrating the volumes of the vent chamber 58, the reaction vials 56 and the pressures within each when in use, the pressure differential across the permeable membrane 57 can be managed and optimized to improve the efficacy of the permeable membrane 57 and to ensure that the pressure differential does not exceed the design limits of the permeable membrane 57.

In some embodiments, the volume of the vent chamber 58 is sufficiently small such that the entry of gas into the vent chamber 58, as discussed above, creates sufficient back pressure so as to eliminate the need for a flow restriction device, such as the permeable membrane 57 or valve 67. In such an embodiment, the design of the vent chamber 58 is such that vent channel 60 turns upward and exits into the vent chamber 58, creating a u-tube hydrostatic effect. The u-tube prevents the gases from migrating back into the reaction vial 56 after they reach the vent chamber 58.

Applying a pressure above ambient to the sample and carrier fluid within the reaction vial 56 provides several benefits. For example, applying a pressure to the sample in the reaction vial 56 increases the boiling temperature of the sample and the carrier fluid. Thus, in the example previously described for Denver, Colo., the unpressurized sample boils at about 97 degrees centigrade, quite close to a selected denaturing temperature of from about 94 degrees centigrade to about 96 degrees centigrade. The sample under pressure, however, boils at a temperature higher and, depending on the pressure, sometimes significantly higher than 97 degrees centigrade. That is, because the boiling temperature is raised significantly away from a desired denaturing temperature, it is possible to forego very accurate and, consequently, very expensive temperature control methods. In so doing, bubbles that might otherwise be inadvertently created by boiling or coming out of solution are not created and, therefore, avoid the issues bubbles pose for optical scanning systems as discussed above.

Another advantage of creating a pressurizable cartridge as disclosed is that higher pressure at which the sample and the carrier fluid is maintained reduces the size of bubbles that are present and reduces the change in the volume of those bubbles as the thermocycling process occurs. As noted above, the change in the volume of the bubbles causes a pumping action by which the sample and carrier fluid may move into and out of the reaction vial by the changing volume of the bubbles. Thus, using pressure to minimize the volume of the bubbles reduces this pumping action that might cause dilution of PCR reagents in the reaction vial 56. In addition, reducing the volume of the bubbles reduces the effect those bubbles have on the optical scanning systems. That is, smaller bubbles will cause less noise in the optical signal used with fluorescence detection systems, as discussed above.

Yet another advantage is that the reaction vials 56 optionally are formed of a thin plastic and shaped with a taper to ensure good contact with the heating/cooling block that is used to heat and cool the reaction vial 56 and the sample therein during the thermocycle process. Holding the sample and carrier fluid at a higher pressure within the reaction vial 56 causes the thin plastic wall 55 (FIG. 11) of the reaction vial 56 to bulge slightly and press more tightly against the heating and cooling block, thereby improving the heat transfer thereto and the efficiency of the thermocycle process.

FIG. 10 depicts the optional use of a sonic transducer 72 in association with the sample assembly. Copending U.S. patent application Ser. No. 11/958,299, filed Dec. 17, 2007 and entitled "Ultrasonic Release of DNA and RNA" is incorporated in its entirety for all purposes by this reference, and discloses methods and apparatus for releasing DNA or RNA from biological materials using sonic energy.

As has been noted, the PCR process operates on DNA. When it is necessary to detect RNA rather than DNA, the RNA must first converted to DNA before PCR can be utilized. Co-owned U.S. patent application Ser. No. 11/733,035, filed Apr. 9, 2007 and entitled "Rapid Reverse Transcription of PCR", and incorporated by reference in its entirely herein, discloses methods and apparatus for use in forming template cDNA from template RNA, and further discloses incorporating the appropriate constituents for this process into a PCR reaction mixture and performing the transcription step prior to the PCR.

Any suitable thermocycler may be used to bring the sample and PCR reaction mixture to the desired PCR target temperatures, but it is currently preferred to use a thermocycler of the type disclosed in copending U.S. patent application Ser. No. 11/697,917, filed concurrently herewith and entitled "Rapid Thermocycler, and which application is incorporated by reference in its entirely herein.

The methods and apparatus of the invention allow for sample handling in a wide variety of form factors that may be optimized in view of any desired number of samples, portability requirements, the type of PCR detection assembly which might be used, the chemical constituents to be utilized, treatment conditions and steps, and other features that will apparent to one of ordinary skill in view of the teachings herein.

It will be appreciated that the drawings used to describe various aspects of exemplary embodiments of the invention are diagrammatic and schematic representations of such exemplary embodiments, and are not limiting of the present invention, nor are they necessarily drawn to scale. Furthermore, specific details set forth in the foregoing description have been given in order to provide a thorough understanding of the present invention, but it will be apparent to one skilled in the art that the present invention may be practiced without these specific details or with different details. In may respects, well-known aspects of PCR and of thermocyclers have not been described in particular detail in order to avoid unnecessarily obscuring the present invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A sample processing module, comprising:
   a PCR assembly, said PCR assembly including at least one PCR reaction vial;
   a sample assembly, said sample assembly being configured to hold a fluid sample therein,
   said sample assembly being attachable to said PCR assembly so as to form a closed system;
   a delivery channel formed in said PCR assembly, said delivery channel being in fluidic communication with said PCR reaction vial and with said sample assembly;
   a pressurization device; said pressurization device being configured to increase a pressure of said fluid sample in said sample assembly and direct at least a portion said fluid sample through said delivery channel to said PCR reaction vial,
   a vent channel in fluidic communication with said PCR reaction vial;
   a vent chamber in fluidic communication with said vent channel; and
   a flow restriction device in fluidic communication with said PCR reaction vial, said flow restriction device being a permeable membrane configured to enable said increase of said pressure to be applied to said fluid sample delivered to said PCR reaction vial, said permeable membrane being located downstream of the PCR reaction vial, downstream of the vent channel and upstream of the vent chamber.

2. The module of claim 1, wherein the vent chamber is sealed to allow it to be pressurized by gasses passing through the permeable membrane.

3. The module of claim 2, wherein said permeable membrane can be at least partially displaced into said vent chamber in response to pressure applied by said vent channel.

4. The module of claim 1, wherein said permeable membrane allows gasses to pass into the vent chamber but retains fluids in the PCR reaction vial.

5. The module of claim 3, further comprising supporting structure, associated with the permeable membrane, the supporting structure operable to limit displacement of the permeable membrane into the vent chamber.

6. The module of claim 5, wherein the supporting structure is at least partially disposed within the vent chamber.

7. The module of claim 1, wherein the PCR reaction vial includes at least one wall formed of a thin plastic, the at least one wall being capable of bulging in response to pressure within the PCR reaction vial.

8. A sample processing module, comprising:
   a sample assembly, said sample assembly being configured to hold a fluid sample therein,
   said sample assembly including a pressurization device configured to increase a pressure of said fluid sample in said sample assembly; and
   a PCR assembly, said PCR assembly including at least one PCR reaction vial, said PCR assembly being configured to receive said sample assembly so as to form a closed system, said PCR assembly including:
   a delivery channel, said delivery channel being in fluidic communication with said PCR reaction vial and with said sample assembly;
   a vent channel in fluidic communication with said PCR reaction vial;
   a flow restriction device; and
   a sealed vent chamber in fluid communication with said vent channel;
   wherein said vent channel is positioned downstream of said PCR reaction device and wherein said flow restriction device is positioned downstream of said vent channel, and wherein said vent chamber is positioned downstream of said flow restriction device, said flow restriction device being configured to enable said increase of said pressure to be applied to said fluid sample delivered to said PCR reaction vial.

9. The module of claim 8, wherein said flow restriction device is a permeable membrane.

10. The module of claim 9, wherein said vent chamber can be pressurized by gasses passing through the permeable membrane.

11. The module of claim 9, wherein said permeable membrane can be at least partially displaced into said vent chamber in response to pressure applied through said vent channel.

12. The module of claim 8, wherein said permeable membrane allows gasses to pass into the vent chamber but retains fluids in the PCR reaction vial.

13. The module of claim 11, further comprising supporting structure, associated with the permeable membrane, the supporting structure operable to limit displacement of the permeable membrane into the vent chamber.

14. The module of claim 13, wherein the supporting structure is at least partially disposed within the vent chamber.

15. The module of claim 8, wherein the PCR reaction vial includes at least one wall formed of a thin plastic, the at least one wall being capable of bulging in response to pressure within the PCR reaction vial.

* * * * *